United States Patent [19]

Hough et al.

[11] Patent Number: 4,774,933

[45] Date of Patent: Oct. 4, 1988

[54] METHOD AND APPARATUS FOR IMPLANTING HEARING DEVICE

[75] Inventors: Jack V. D. Hough, Yukon, Okla.; Paul DiCarlo, Jacksonville, Fla.

[73] Assignee: Xomed, Inc., Jacksonville, Fla.

[21] Appl. No.: 122,590

[22] Filed: Nov. 17, 1987

Related U.S. Application Data

[63] Continuation of Ser. No. 052,180, May 18, 1987, abandoned, which is a continuation of Ser. No. 734,619, May 16, 1985, abandoned.

[51] Int. Cl.$^4$ .................................. H04R 25/00
[52] U.S. Cl. .................................. 600/25; 128/303 R; 128/92 VT; 381/68.3

[56] References Cited

U.S. PATENT DOCUMENTS

| | | | |
|---|---|---|---|
| 2,402,392 | 6/1946 | Goldschmidt | 179/107 |
| 3,209,081 | 9/1965 | Ducote et al. | 179/107 BC |
| 3,712,962 | 1/1973 | Epley | 179/107 R |
| 3,764,748 | 10/1973 | Branch et al. | 179/107 E |
| 3,870,832 | 3/1975 | Frederickson | 179/107 E |
| 3,882,285 | 5/1975 | Nunley et al. | 179/107 E |
| 4,052,754 | 10/1977 | Homsy | 623/10 |
| 4,150,262 | 4/1979 | Owo | 179/107 BC |
| 4,284,856 | 8/1981 | Hochmair et al. | 179/107 BC X |
| 4,338,926 | 7/1982 | Kummer et al. | 623/16 X |
| 4,352,960 | 10/1982 | Dormer et al. | 179/107 BC |
| 4,357,497 | 11/1982 | Hochmair et al. | 179/107 BC X |
| 4,388,921 | 6/1983 | Sutter et al. | 623/16 X |
| 4,419,995 | 12/1983 | Hochmair et al. | 128/419 R |
| 4,498,461 | 2/1985 | Hakansson | 179/107 BC |
| 4,532,930 | 8/1985 | Crosby et al. | 179/107 BC X |
| 4,541,429 | 9/1985 | Prosl et al. | 623/11 X |
| 4,606,329 | 8/1986 | Hough | 381/68.3 X |
| 4,612,915 | 9/1986 | Hough et al. | 381/68.3 X |

FOREIGN PATENT DOCUMENTS

| | | |
|---|---|---|
| 1961531 | 7/1970 | Fed. Rep. of Germany ........ 623/16 |
| 1616149 | 2/1978 | Fed. Rep. of Germany . |
| 2044870 | 5/1978 | Fed. Rep. of Germany . |
| 553955 | 6/1943 | United Kingdom . |
| 2137884A | 10/1984 | United Kingdom .................. 623/16 |

OTHER PUBLICATIONS

Tjellstrom et al.–Direct Bone Anchorage of External Hearing Aids–Jan. 1983–pp. 59–63–Journal Biomed Engineering, vol. 5.

Robinson et al.–Bone Conduction Speech Discrimination–Apr. 1977–pp. 238–240–Arch Otolaryngol–vol. 103.

Hakansson et al.–Hearing Thresholds with Direct Bone Conduction Versus Conventional Bone Conduction–1984–Scand Audiol 13–pp. 3–13.

Primary Examiner—Ira S. Lazarus
Assistant Examiner—Richard R. Cole
Attorney, Agent, or Firm—Arthur G. Yeager

[57] ABSTRACT

A bone conduction hearing device in the form of a magnetic disk is implanted and fastened to the temporal bone by a screw thread connection. Apparatus includes instruments for accurately drilling and tapping a hole in the temporal bone, and a wrench for tightening the magnetic disk hearing device against the bone.

16 Claims, 3 Drawing Sheets

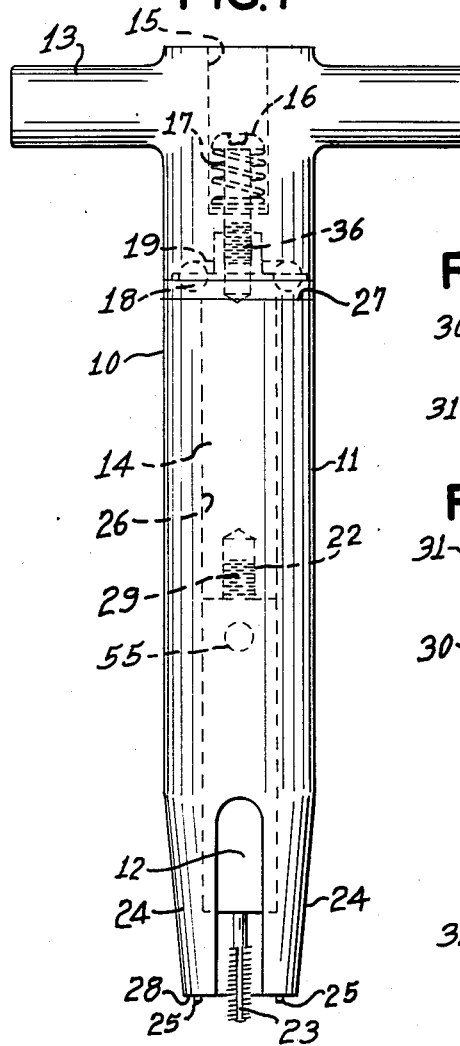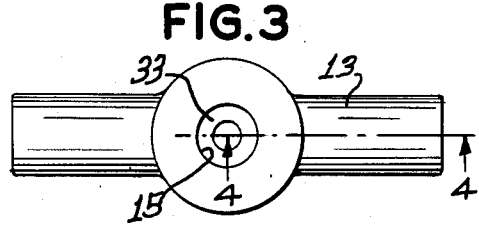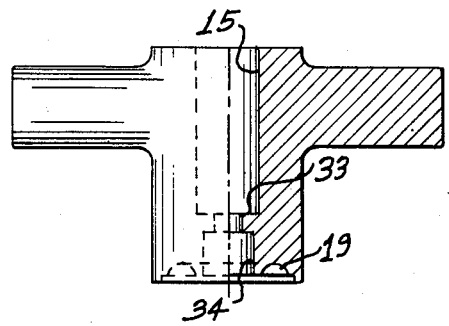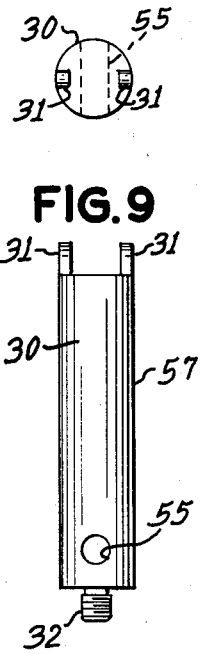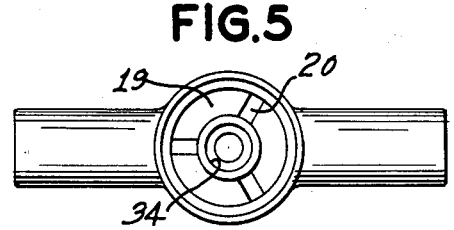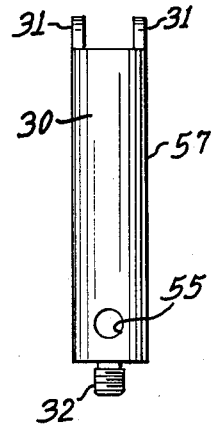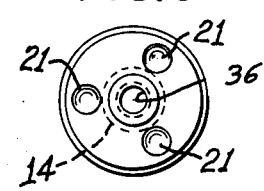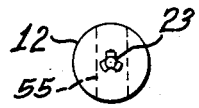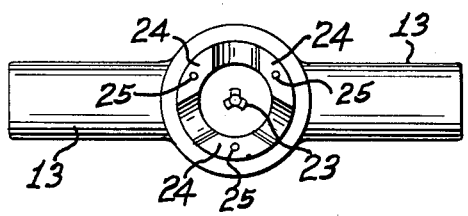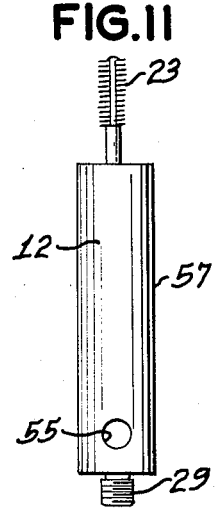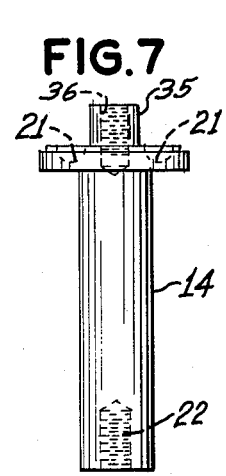

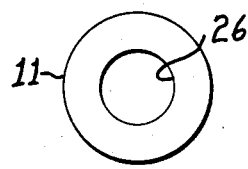
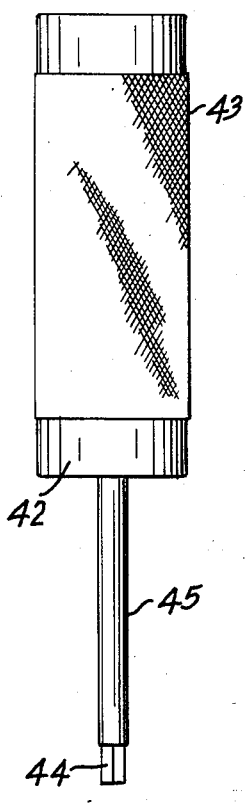
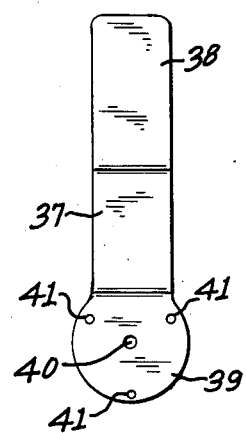
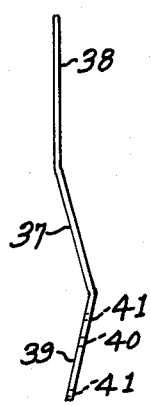
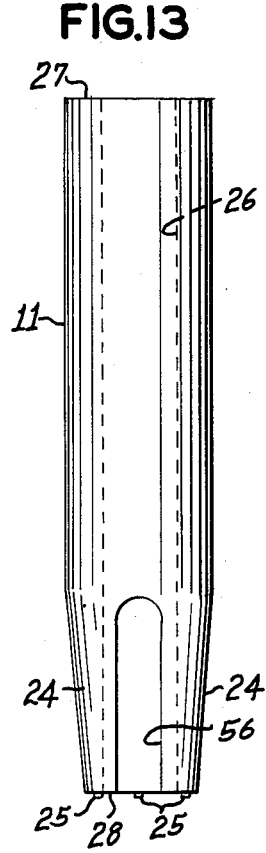
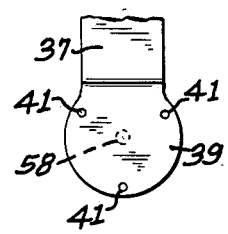
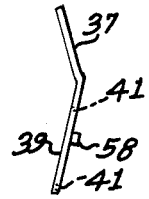
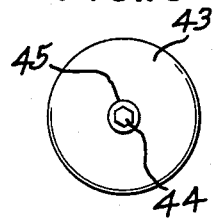
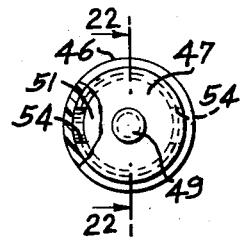
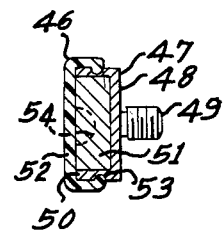
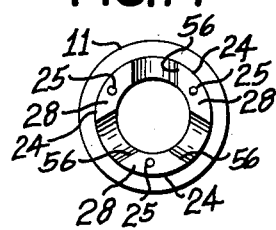

U.S. Patent  Oct. 4, 1988  Sheet 3 of 3  4,774,933
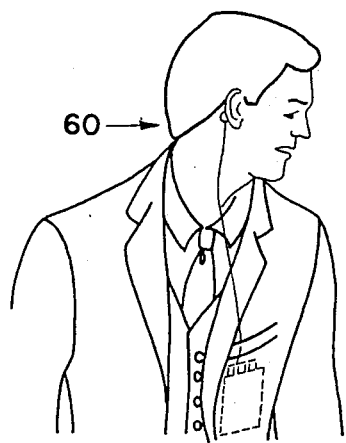
FIG 23
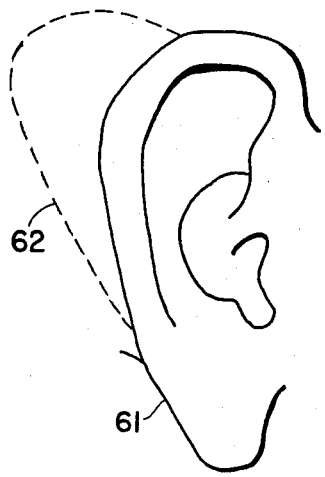
FIG 24
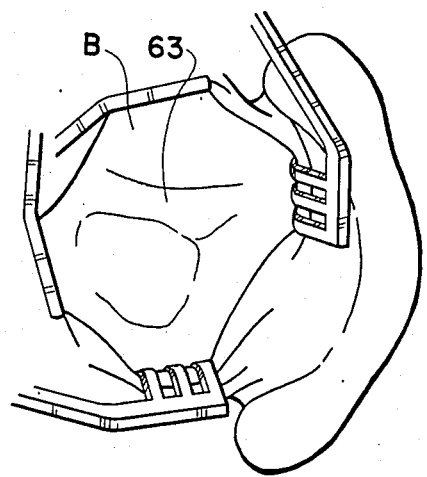
FIG 25
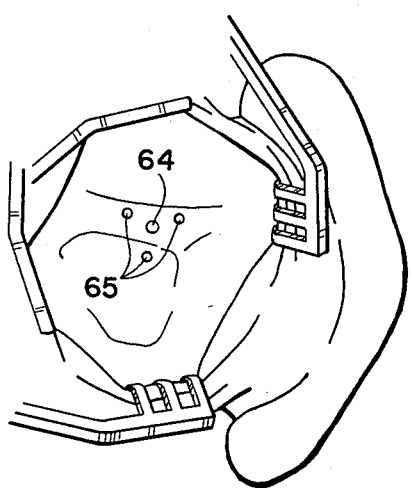
FIG 26
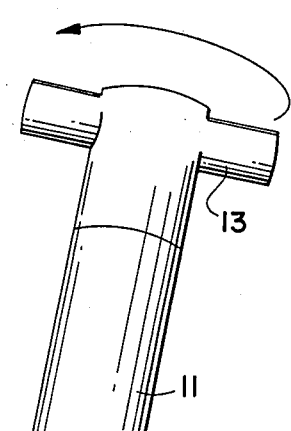
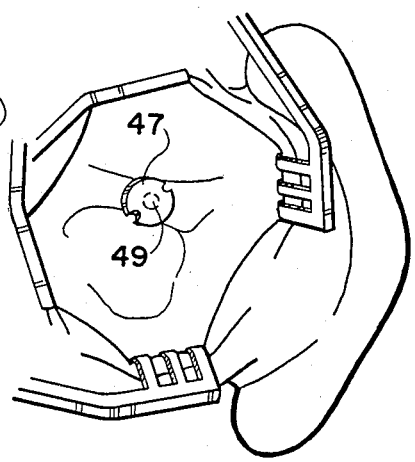
FIG 28
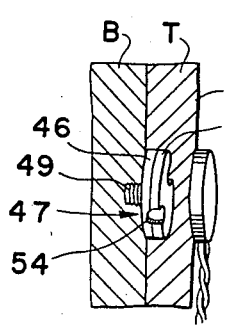
FIG 30
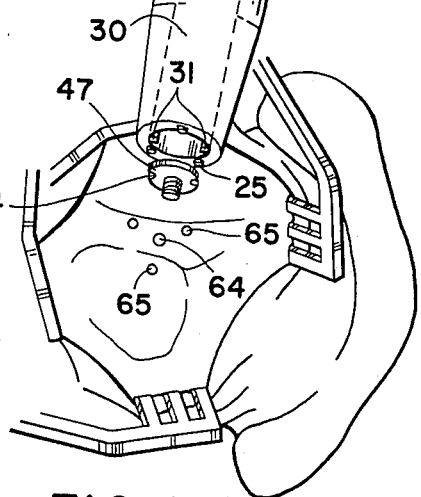
FIG 27
FIG 29

METHOD AND APPARATUS FOR IMPLANTING HEARING DEVICE

This is a continuation of co-pending application Ser. No. 07/052,180 filed on May 18, 1987, which was a continuation of application Ser. No. 06/734,619 filed on May 16, 1985 both of which are now abandoned.

BACKGROUND OF THE INVENTION

Many hearing impaired individuals who are able to benefit from sound amplification utilize conventional air conduction hearing aids. However, a significant number of patients who could benefit from sound amplification are unable to utilize air conduction aids due to chronic inflammation or infection, as well as congenital or acquired malformation of the external ear canal and/or middle ear. For those patients that cannot be fitted with a conventional air conduction hearing aid, a bone conduction hearing device is sometimes recommended.

Bone conduction is a well known concept for sound amplification, dating back to the 16th century. Modern bone conduction hearing devices are available using either a steel headband or tight fitting eyeglass frames to press a sound transducer firmly against the patient's skull. The sound amplification electronics are mounted in a small "box" worn on the patient's clothing or within the eyeglass frames. There are, however, several disadvantages to this type of amplification. The soft tissues interposed between the sound transducer and the bone impair the direct transmission of sound to the bone, which can lead to distortion and poor sound fidelity. In addition, these devices of necessity generate a great deal of pressure against the soft tissue and the resultant discomfort and pain lead many patients to discontinue the use of the device.

A group of researchers in Sweden has attempted to accomplish this goal by anchoring a metal fixture in the patient's skull and routing this fixture through the skin (percutaneously) behind the ear. A bone conduction transducer is then fitted to the external projection of the fixture. This procedure raises serious concerns about the possibility of infection around the percutaneous connection and the possibility of patient injury in the event of trauma to the external projection of the bone fixture.

An improved hearing device component for subcutaneous attachment to the skull is described and claimed in copending application Ser. No. 674,176 filed Nov. 23, 1984, now abandoned, but continued under 35 USC 120 as application Ser. No. 737,188 filed May 23, 1985, now U.S. Pat. No. 4,612,915, granted Sept. 23, 1986.

It is an object of this invention to provide a method for implanting subcutaneously a hearing device component against the skull of a patient. It is still another object to provide a surgical kit for use in such an implantation procedure. Still other objects will appear in the more detailed description which follows.

BRIEF DESCRIPTION OF THE INVENTION

This invention relates to a method and apparatus for implanting a hearing device component. The method includes implanting a magnetic disk means on the temporal bone to enhance sound transmission, the method comprising the steps of:

(1) making an incision behind the ear and exposing the linea temporalis of the temporal bone;

(2) drilling and tapping a hole approximately 4 mm. deep in a substantially flat surface of the temporal bone;

(3) attaching a magnetic disk means having a flat lower surface to the temporal bone by a screw means threaded into the drilled and tapped hole of step (2).

(4) tightening the screw means to cause the flat lower surface of the magnetic disk means to lie snugly against the flat surface of the temporal bone; and (5) closing the incision with the magnetic disk means implanted abutting against the temporal bone.

The apparatus of this invention relates to a surgical kit for use in implanting a magnetic disk means having a depending screw means attachable to the temporal bone, the kit comprising:

(1) a template having a means for indexing the template over a central drilled hole in the temporal bone and a plurality of spaced openings around the periphery thereof for locating guide holes to be drilled into the bone;

(2) an elongated guide having opposite end portions and a central cylindrical passageway extending between the end portions and aligned with the longitudinal axis of the guide, a plurality of spaced legs projecting from one end portion, each leg having a short peg depending therefrom in an axial direction adapted to mate with and substantially fill one guide hole;

(3) a wrench having a shaft portion snugly and rotatably fitting within the central cylindrical passageway, and a head portion extending above the other end portion of the guide adapted to be manually gripped for rotation thereof;

(4) a plurality of extension members each separately attachable to the shaft portion and rotatable within the passageway, one of the members having a cutting end portion for tapping the drilled hole in the temporal bone, another of the members being releasably engageable with the magnetic disk means for threadedly attaching the screw means into the tapped hole in the temporal bone; and (5) a burr for drilling the central drilled hole; and (6) a burr for drilling the guide holes.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the medical instrument of this invention;

FIG. 2 is a bottom plan plan view of the instrument shown in FIG. 1;

FIG. 3 is a top plan view of the handle portion of the instrument;

FIG. 4 is a front elevation, partially in cross section of the handle portion shown in FIG. 3;

FIG. 5 is a bottom plan view of the handle portion shown in FIGS. 3 and 4;

FIG. 6 is a top plan view of the shank portion of the instrument;

FIG. 7 is a front elevational view of the shank portion shown in FIG. 6;

FIG. 8 is a bottom plan view of the extension member employed to fasten the magnetic disk to the temporal bone;

FIG. 9 is a front elevational view of the extension member of FIG. 8;

FIG. 10 is a bottom plan view of the extension member employed to tap a hole in the temporal bone;

FIG. 11 is a front elevational view of the extension member of FIG. 10;

FIG. 12 is a top plan view of the guide of the instrument;

FIG. 13 is a front elevational view of the guide shown in FIG. 12;

FIG. 14 is a bottom plan view of the guide shown in FIGS. 12 and 13;

FIG. 15 is a front elevational view of the torque adjusting wrench of this invention;

FIG. 16 is a bottom plan view of the wrench of FIG. 15;

FIG. 17 is a front elevational view of the template of this invention;

FIG. 18 is a side elevational view of the template of FIG. 17.

FIG. 19 is a front elevational view of an alternate embodiment of the template of FIGS. 17-18;

FIG. 20 is a side elevational view of the template of FIG. 19;

FIG. 21 is an enlarged top plan view of the magnetic disk implant employed in this invention;

FIG. 22 is a cross-sectional view taken along line 22—22 of FIG. 21.

FIG. 23 is a perspective view of a person illustrating the use of a hearing system attached to the person in accord with the method of this invention;

FIG. 24 is a fragmentary elevation view illustrating the incision area of the skull of a person;

FIG. 25 is a view similar to FIG. 24 showing the incision opened to expose the *linea temporalis;*

FIG. 26 is a view similar to FIG. 25 showing a drilled central hole and spaced guide holes;

FIG. 27 is a view similar to FIG. 26 showing a portion of the hearing device being secured by a wrench within a guide insertable into the spaced guide holes;

FIG. 28 is a view similar to FIG. 27 showing the portion of the hearing device secured;

FIG. 29 is a view similar to FIG. 24 illustrating the incision after closure thereof; and FIG. 30 is an enlarged fragmentary view illustrating the hearing device illustrated in FIG. 23 with the implanted portion being magnetically coupled to the outer removable portion.

DETAILED DESCRIPTION OF THE INVENTION

The medical instrument of this invention comprises a set of instruments for locating, drilling, and tapping a hole in the temporal bone, and for attaching a magnetic disk snugly against the bone for use in a hearing aid. In FIGS. 1 and 2 the components of the instrument are assembled for use in tapping a hole. The various components of the instrument are shown separately in FIGS. 3-14. The magnetic disk implant is shown FIGS. 21-22. Two tools employed in conjunction with the instrument are shown in FIGS. 15-20.

With specific reference to FIGS. 1-14 the medical instrument 10 will be described. An outer guide member 11 with a lengthwise axial bore 26 has an upper end 27 and a lower end 28 which fall in two parallel planes generally perpendicular to the axis of bore 26. Handle portion 13 is attached to shank portion 14 that is rotatably journaled in bore 26. Different designs of extension members are attached to the bottom of shank portion 14 by way of threaded hole 22. In FIG. 1 extension member 12 is shown with a tapping head 23 that extends slightly below lower end 28. In actual use, lower end 28 rests on the exposed temporal bone and tapping head 23 is then in a position to be lowered and rotated by rotation of handle portion 13 to cut a threaded hole into the bone. Extension member 12 has a threaded shank 29 to mate with threaded hole 22 in the bottom of shank portion 14.

Handle portion 13 may be integrally a part of shank portion 14 or these two portions may, as is shown in FIG. 1, be joined through an adjustable slip mechanism that serves the purpose of providing an adjustable maximum torque which can be applied by handle portion 13 to turn shank portion 14. It will be appreciated that in surgical operations of the type involved here, it is extremely important that a tapped hole in the skull not be destroyed by applying too much torque when screwing a component into that tapped hole. To prevent such an occurrence the instrument of FIG. 1 provides a mechanism that can be adjusted to slip when a selected torque is applied. The mechanism comprises a spring loaded ball bearing connection. Ball bearings 18, preferably three or more for stable operating characteristics, are seated in hemispherical seats 21 in the top of shank portion 14 and a circular groove 19 in handle portion 13. Cross grooves 20, one per ball bearing, are positioned in radial directions. The spacing between cross grooves 20 and between seats 21 is the same so that for handle portion 13 and shank portion to be locked together, each ball bearing will rest in a seat 21 with its upper surface engaged in a cross groove 20. Handle portion 13 and shank portion 14 are joined together by screw 16 and spring 17 bearing against ledge 33 in counterbore 15 of handle portion 13. Screw 16 is threaded into tapped hole 36 in upper shank 35 of shank portion 14. The action of spring 17 is to bias handle portion 13 to press against ball bearings 18 and shank portion 14. If the bias of the spring is small it requires only a small torque applied to handle portion 13 to cause ball bearings 18 to become disengaged from cross grooves 20 and to roll in groove 19. This provides, in effect, a slippage wherein handle portion 13 turns while shank portion 14 does not turn. As screw 16 is tightened farther and farther into hole 36, spring 17 exerts more and more force to hold ball bearings 18 in cross grooves 20, requiring greater and greater torque to cause slippage between handle portion 13 and shank portion 14. Eventually at full tightening of screw 16, handle portion 13 and shank portion 14 are locked together as through the two portions were of one integral piece.

At the bottom end 28 of guide 11 there are three cut out portions 56 forming three legs 24. Cut out portions 56 provide means for the surgeon to see exactly how tapping head 23 is functioning. Pegs 25 project downwardly from legs 24 and are fitted into corresponding holes drilled in the temporal bone to provide a precise location and positive seating for guide 11 when lower end 28 is resting on the temporal bone of the patient.

Extension members are attached to the bottom of shank portion 14 by screw thread attachment. FIGS. 10 and 11 show extension member 12 with a tapping head 23. The shank portion 57 of member 12 is machined to fit slideably within bore 26 of guide 11 with close tolerance therebetween. Tapping head 23 is made a precise length such that it will extend below lower end 28 of guide 11 the exact amount of the depth desired to be tapped in the temporal bone. It has been found preferable to employ two extension members with different diameter tapping heads. The first to be used is smaller in diameter than the final tap. For example, if the final tap is approximately 4 mm. in diameter, the preliminary tap is about 2.5 mm. in diameter. A more precise tapping of bone can be accomplished with less chance of shattering any of the bone by using two such taps. Furthermore, the torque required to tap a small hole into a final large diameter thread in a single operation is too great in most instances to be done easily by the surgeon turning the tap by hand.

Another type of extension member is shown in FIGS. 8 and 9. This extension member 30 is substantially the same with respect to shank 57 and threaded shank 32 as the corresponding portions of extension member 12 (FIGS. 11 and 12). The operating end of extension member 30 has two diametrically opposite prongs 31 which are positioned and shaped to engage two respective recesses 54 on magnetic disk 46 of FIGS. 21 and 22. Extension member 30 is employed to screw the magnetic disk implant 46 into the tapped hole in the temporal bone, which step may employ the torque-slippage mechanism described above so as to tighten the implant snugly against the skull but not to use so much torque as to cause damage to the threads in the bone. In each extension member there is a lateral passageway 55 adjacent the upper end thereof. This passageway is provided so the surgeon may, if desired, insert a cross piece, such as shaft 45 of the wrench of FIG. 15, to serve as a handle for turning the extension member, e.g., to unscrew the tapping head of the member of FIG. 11 from the tapped hole in the temporal bone.

In FIGS. 3-7 the individual components of the handle portion 13 and the shank portion 14 are seen in detail. Handle portion 13 has a central axial passageway which comprises upper bore 15 and lower bore 34 joined together by a passageway of smaller diameter than either of bores 15 or 34 and yet large enough to allow the shank of screw 16 to pass therethrough. Groove 19 forms a race for ball bearings 18. Upper shank 35 fits into bore 34 when the two components handle portion 13 and shank portion 14 are joined as shown in FIG. 1.

Guide 11 is shown in FIGS. 12-14 as a cylindrical tube with a central axial bore 26 that forms a journal for shank portion 14 and extension members 12 or 30. The lower portion of guide 11 is preferably tapered to provide a small lower end 28 which may be seated on the exposed temporal bone with pegs 25 fitting into corresponding drilled holes in the bone.

FIGS. 15 and 16 show a wrench 42 that may be used to tighten or loosen screw 16 (FIG. 1) to adjust the slippage torque between handle portion 13 and shank portion 14. A convenient size knurled handle 43 is attached to a shank of sufficient length to extend into bore 15 of handle portion 13. A hex head tip 44 is shown to engage a hex head (Allen head) recess in screw 16. If screw 16 were fashioned with a slot instead of a hex head recess, tip 44 could be a blade screwdriver head. Any other cooperating recesses and tips can be employed, e.g., Phillips head or square Allen head.

FIGS. 17-20 show templates that are employed in performing the implant operation of this invention. The purpose of the template is to locate the holes that are drilled in the temporal bone that will engage pegs 25 on the lower end 28 of guide 11. Once a location has been selected by the surgeon for attaching the implant a hole is drilled at that point. The template is then placed over the hole in the bone with central hole 40 directly over the hole in the bone. Guide holes 41 are then marked for drilling. This assures that guide 11 will be placed precisely over the hole in the bone so that tapping of the hole can take any convenient shape. The shape shown here includes guide portion 39 to be placed flat against the temporal bone and a handle portion 38 for easy gripping by the surgeon or his assistant. The alternative structure shown in FIGS. 19 and 20 merely replaces central hole 40 with a central peg 58 of an appropriate size to be pressed snugly into the previously drilled hole in the temporal bone. This alternative eliminates any possibility of slight visual misalignment of the hole 40.

The implant 46 itself is shown in FIGS. 21 and 22 and is more clearly described in the above copending patent application, now U.S. Pat. No. 4,612,915. The implant includes a base 47 holding a disk magnet 51 coated with a silicone covering 52. Base 47 must be a good sound conductor and, therefore, preferably is metal, such as Titanium. Base 47 has a flat bottom surface 48 and a central threaded shank 49 projecting outwardly therefrom. The upper portion 50 of base 47 is cup-shaped to form a recess for holding disk magnet 51. A preferred magnet material is a combination of cobalt and a rare earth material, such as samarium. These materials make long lasting permanent magnets admirably suited for this application. Such materials as cobalt and the rare earths are not biocompatible and must therefore be covered with a medically inert material so as to be a suitable implant. The magnet is preferably coated with a nonpermeable biocompatible material such as "Paralene", "Teflon", etc. Medical grade silicone is then employed as a coating 52 covering all exposed parts of the coated magnet 51 and is sealed to the sidewall of titanium base 47. Bottom surface 48 must not be covered with silicone because it would materially decrease the sound conduction property of the metal. One method of making a tight seal is shown here as a groove 53 around the outside of the sidewall of base 47. Silicone cover 52 is molded to fit into groove 53 and thereby be held tightly in place.

FIGS. 23-30 illustrate the method employed in this invention for enhancing the hearing of the person or patient 60 shown in FIG. 23 with the hearing system installed.

The method employed in this invention includes:

(1) An incision is made about 2 inches in diameter behind the ear 61 over the temporal bone of the patient's skull, as illustrated generally by broken line 62 in FIG. 24. The incision is made directly to the periosteum. After suitable hemostasis is obtained, the soft tissues T are lifted to expose the bone B, as shown in FIG. 25. The *linea temporalis* 63 of the temporal bone B is exposed and is smoothed at the point selected for the implant. A hole 64, as generally illustrated in FIG. 26, is drilled at this point with a burr of about 3.2 mm. diameter and 4 mm. deep. This will eventually be the attachment for fastening the implant. The template 37 is then placed over the drilled hole 64 so as to locate through guide holes 41 the places to be drilled. A burr 1.5 mm. in diameter is used to drill spaced holes 65 at the marked locations.

(2) Guide 11 is then placed over the drilled central hole 64 in the bone B with pegs 25 fitting into the spaced holes 65 drilled in the bone at the location produced by guide holes 41. The instrument of FIG. 1 is assembled with extension member 12 attached having a tapping head 23 of a size smaller than the desired final diameter.

(3) The drilled hole 64 in the bone is carefully tapped by turning handle portion 13 until tapping head 23 has proceeded to its full extent beyond lower end 28 of guide 11. The turning is then reversed to back out tapping head 23 from the tapped hole 64 in the bone B.

(4) Extension member 12 is then replaced with another similar extension member except that its tapping head is of the final desired diameter. The tapped hole is then retapped to the final desired size by turning handle portion 13 until the tapping head reaches its full extent below lower end 28 of guide 11. The turning is then reversed to back out the tapping head from the fully tapped hole 64. If the reversed turning of handle portion 13 does not remove tapping head from the tapped hole 64, but rather separates extension member 12 from shank portion 14 at threaded connection 22/29, shank 45 of wrench 43 can be inserted into hole 55 on shank 57 and twisted to loosen tapping head 23 from the tapped hole in the temporal bone.

(5) Extension member 30 is then attached to shank portion 14 and a first portion in the form of a magnetic disk means 47 is attached thereto by inserting prongs 31 into recesses 54. The lower end of extension member 30 adjacent prongs 31 may have previously been made to be attracted to magnetic forces so as to assist in holding magnetic disk means 47 onto the end of extension member 30. Screw 16 is adjusted to provide the desired slip/torque relationship between handle portion 13 and shank portion 14. Magnetic disk means 47, as illustrated in FIG. 27, is then threaded into the tapped hole 64 in the bone B to a desired torque. This should be such that the maximum area of bottom surface 48 is in contact with the temporal bone B in the area of the *linea temporalis* 63, as generally shown in FIG. 28.

(6) The instrument is then removed from the area of the operation and the incision 62 is closed after the soft tissue T and skin S are stitched, as illustrated in FIG. 29, leaving the magnetic disk means 47 as an implant.

A suitable commercially available battery operated system is employed to translate external sound waves into electromagnetic waves by a second member in the form of an output transmitter portion 66, as described more fully in the above copending application, now U.S. Pat. No. 4,612,915, which are received by the implanted magnet and changed to appropriate vibrations which are conducted through the temporal bone to the inner ear.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A method for implanting a magnetic disk means on the mastoid bone to enhance sound transmission, the method comprising the steps of:
   (1) making an incision behind the ear and exposing the *linea temporalis* of the temporal bone;
   (2) drilling a hole in a substantially flat surface of the temporal bone;
   (3) tapping the drilled hole to provide internal screw threads therein;
   (4) attaching a magnetic disk means having a flat lower surface to the temporal bone by a screw means threaded into the tapped hole of step (3);
   (5) tightening the screw means to cause the flat lower surface of the magnetic disk means to lie snugly against the flat surface of the temporal bone; and
   (6) closing the incision with the magnetic disk means implanted abutting against the temporal bone.

2. The method of claim 1 wherein between steps (1) and (2), further comprising step (7) machining the exposed surface of the temporal bone to produce a small flat surface.

3. The method of claim 1 wherein step (2) includes the steps of (7) drilling a small central hole, and (8) drilling a plurality of small guide holes spacedly about the central hold to receive an identical plurality of pins to support a guide means for tapping of the drilled hole of step (2).

4. The method of claim 1 wherein step (5) includes the step of (7) rotating a wrench means to provide a selected maximum torque to the screw means in attaching the magnetic disk means to the temporal bone.

5. The method of claim 1 wherein step (3) includes the step of (7) tapping the drilled hole to a preliminary diameter, and (8) retapping the tapped hole to the final desired diameter and thread size.

6. A method for implanting a magnetic disk means on the mastoid bone to enhance sound transmission, the method comprising the steps of:
   (1) making an incision behind the ear and exposing the *linea temporalis* of the temporal bone;
   (2) drilling and tapping a hole in a substantially flat surface of the temporal bone;
   (3) attaching a magnetic disk means having a flat lower surface to the temporal bone by a screw means threaded into the drilled and tapped hole of step (2);
   (4) tightening the screw means to cause the flat lower surface of the magnetic disk means to lie snugly against the flat surface of the temporal bone; and
   (5) closing the incision with the magnetic disk means implanted abutting against the temporal bone.

7. A method for enhancing hearing comprising the steps of:
   making an incision and exposing a portion of patient's skull;
   subcutaneously implanting into the exposed skull portion a first member including a magnetic portion and capable of receiving electromagnetic signals and generating vibrations;
   securing the first member in contact with and to the skull portion;
   closing the incision;
   magnetically securing a second member capable of transmitting electromagnetic signals to the magnetic portion of the first member; and
   transmitting electromagnet signals transcutaneously from the first member to the second member and generating vibrations in the skull portion in contact with the first member which are conducted to the patient's inner ear.

8. The method of claim 7 wherein the first member includes a bone screw and the step of securing includes drilling a hole into the skull portion and screwing a portion of the bone screw into the hole.

9. The method of claim 7 wherein the first member includes a bone screw and the step of securing includes the steps of drilling a hole and tapping the hole with screw threads in the skull portion and screwing a portion of a bone screw into the tapped hole.

10. The method of claim 9 wherein the step of drilling further includes drilling a central hole and plurality of predeterminedly spaced guide holes about the central hole, supporting a guide member in the guide holes, and guiding a tapping member with the guide member for tapping the central hole.

11. The method of claim 9 wherein the step of tapping includes tapping the drilled hole to a preliminary diameter and subsequently retapping the tapped hole to a final diameter.

12. The method of claim 9 wherein the exposed skull portion is a temporal bone and the magnetic portion includes a magnetic disk attached to the bone screw and the step of securing includes abutting the magnetic portion against the temporal bone.

13. The method of claim 12 wherein the step of securing includes using a tool having a selected maximum torque to screw the bone screw to the temporal bone.

14. The method of claim 13 wherein the step of securing includes rotating a wrench to produce the selected maximum torque to screw the bone screw to the temporal bone.

15. The method of claim 12 further comprising machining the temporal bone to produce an exposed flat surface to be contacted by the magnetic portion.

16. The method of claim 15 wherein the step of securing includes tightening the bone screw and magnetic portion of the first member against the machined flat surface of the temporal bone.

* * * * *